United States Patent
Yang et al.

(10) Patent No.: US 10,729,816 B2
(45) Date of Patent: Aug. 4, 2020

(54) CUSTOMIZED LOAD-BEARING AND BIOACTIVE FUNCTIONALLY-GRADED IMPLANT FOR TREATMENT OF OSTEONECROSIS

(71) Applicant: The Board of Trustees of the Leland Stanford Junior University, Palo Alto, CA (US)

(72) Inventors: Yunzhi Yang, Redwood City, CA (US); Stuart B. Goodman, Los Altos, CA (US); Yaser Shanjani, Milpitas, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 93 days.

(21) Appl. No.: 15/559,550

(22) PCT Filed: Mar. 18, 2016

(86) PCT No.: PCT/US2016/023290
§ 371 (c)(1),
(2) Date: Sep. 19, 2017

(87) PCT Pub. No.: WO2016/154063
PCT Pub. Date: Sep. 29, 2016

(65) Prior Publication Data
US 2018/0043062 A1 Feb. 15, 2018

Related U.S. Application Data

(60) Provisional application No. 62/135,725, filed on Mar. 20, 2015.

(51) Int. Cl.
*A61L 27/58* (2006.01)
*A61L 27/56* (2006.01)
*A61B 17/74* (2006.01)
*A61F 2/36* (2006.01)
(Continued)

(52) U.S. Cl.
CPC ............ *A61L 27/58* (2013.01); *A61B 17/742* (2013.01); *A61F 2/3609* (2013.01); *A61L 27/10* (2013.01);
(Continued)

(58) Field of Classification Search
CPC ............ A61F 2002/30011; A61F 2002/30014
See application file for complete search history.

(56) References Cited

U.S. PATENT DOCUMENTS 4,997,444 A * 3/1991 Farling ............... A61F 2/30965
623/23.51
6,149,688 A * 11/2000 Brosnahan ................ A61F 2/28
623/23.5
(Continued)

FOREIGN PATENT DOCUMENTS

EP 2696806 A1 2/2014

OTHER PUBLICATIONS

Determination of cortical bone porosity and pore size distribution using a low field pulsed NMR approach, Wang et al. 2003 Journal of Orthopaedic Research 21:312-319.

*Primary Examiner* — Bruce E Snow
*Assistant Examiner* — Melissa A Hoban
(74) *Attorney, Agent, or Firm* — Lumen Patent Firm

(57) ABSTRACT

An engineered medical device for treatment of osteonecrosis is provided where the size, porosity and ceramic content of the device can be personalized based on an individual patient's anatomical and physiological condition. The device distinguishes different segments mimicking anatomically-relevant cortical and cancellous segments, in which the cortical segments of the device can sustain mechanical loading, and the cancellous segment of the device can promote bone ingrowth, osteogenesis and angiogenesis.

22 Claims, 15 Drawing Sheets

(51) Int. Cl.
*A61L 27/10* (2006.01)
*A61L 27/12* (2006.01)
*A61L 27/18* (2006.01)
*A61L 27/54* (2006.01)
*A61F 2/30* (2006.01)

(52) U.S. Cl.
CPC .............. *A61L 27/12* (2013.01); *A61L 27/18* (2013.01); *A61L 27/54* (2013.01); *A61L 27/56* (2013.01); *A61F 2/30942* (2013.01); *A61F 2002/30011* (2013.01); *A61F 2002/30062* (2013.01); *A61F 2002/30224* (2013.01); *A61F 2002/30985* (2013.01); *A61F 2002/3611* (2013.01); *A61F 2310/00179* (2013.01); *A61F 2310/00293* (2013.01); *A61L 2300/414* (2013.01); *A61L 2430/02* (2013.01)

(56) References Cited

U.S. PATENT DOCUMENTS

| | | | |
|---|---|---|---|
| 6,319,255 B1 | 11/2001 | Grundei | |
| 6,673,075 B2 * | 1/2004 | Santilli | A61B 17/1757 623/17.16 |
| 6,767,369 B2 | 7/2004 | Boyer, II | |
| 6,913,623 B1 * | 7/2005 | Zhu | A61F 2/30734 623/23.15 |
| 8,486,143 B2 | 7/2013 | Laurencin | |
| 2002/0173850 A1 | 11/2002 | Brodke | |
| 2003/0114936 A1 | 6/2003 | Sherwood | |
| 2003/0135214 A1 | 7/2003 | Fetto | |
| 2010/0137990 A1 | 6/2010 | Apatsidis | |
| 2011/0052660 A1 | 3/2011 | Yang | |

\* cited by examiner

FIG. 11A
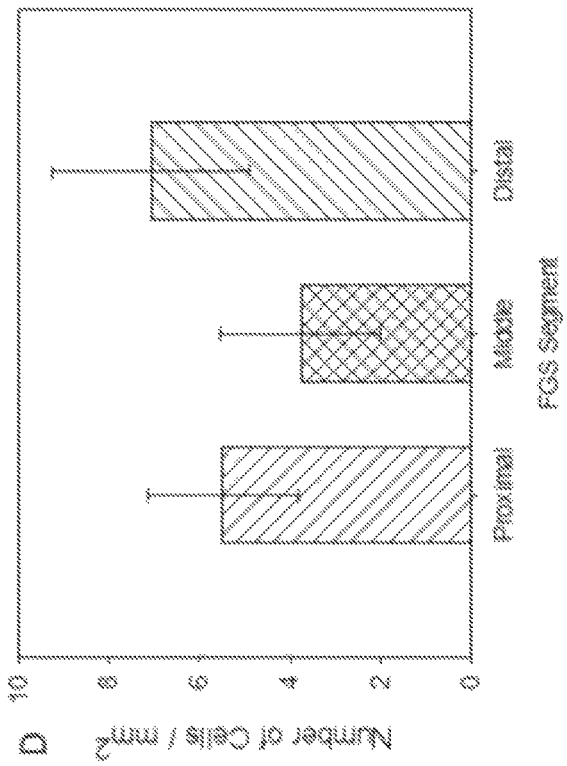
FIG. 11B
FIG. 11D
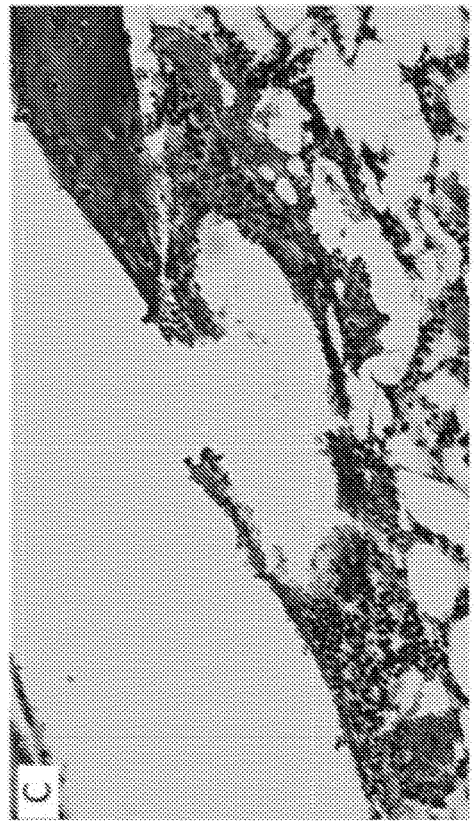
FIG. 11C

US 10,729,816 B2

CUSTOMIZED LOAD-BEARING AND BIOACTIVE FUNCTIONALLY-GRADED IMPLANT FOR TREATMENT OF OSTEONECROSIS

FIELD OF THE INVENTION

This invention relates to devices and methods for preventing progression of osteonecrosis at its early stage. In particular, the invention relates to an implant for reconstruction of the osteonecrotic area.

BACKGROUND OF THE INVENTION

Osteonecrosis of the hip (ONH) is a debilitating disease that is increasing in incidence worldwide and frequently progresses to collapse of the femoral head and osteoarthritis that necessitates total hip replacement. In the early stages of ONH, various medical and surgical treatments to preserve the integrity of the femoral head including pharmacological agents such as statins and anticoagulants, electromagnetic therapy, weight reduction, protected weight bearing and range of motion exercises have been attempted with limited success and have not prevented collapse or provided lasting improvement. Alternatively, surgical treatments such as core decompression of the necrotic segment are often performed to relieve pain prevent progression at the early stages of ONH, prior to femoral head collapse. However a wide range of the success rates have been reported from 20-70% for the early (pre-collapse) stages. Maintenance of sphericity of the patient's own femoral head requires both mechanical and biological strategies to withstand intermittent loading and, at the same time, reconstitute the necrotic femoral bone segment. To prevent the collapse of the femoral head after core decompression, the removed necrotic tissue could be filled by a graft or implant to facilitate reconstruction of the necrotic area.

A vascularized fibula graft is one current clinical option, but it suffers from several limitations including pain associated with graft harvesting, availability of sufficient transplantable bone, and the possibility of infection as well as donor site morbidity. Currently, the implant manufacturer Zimmer supplies a porous tantalum metal implant as a treatment for early stage ONH. However, the tantalum metal implant will remain in the proximal femur region for the patient's lifespan. Furthermore, studies have reported no evidence of vascular invasion and minimal bone ingrowth (only 1.9%) in such implants, much less than the mean density (26.2%) of adjacent femoral head trabecular bone. A continuous shell of new cortical bone forms around the tantalum implant that blocks vascular and cancellous invasion. This nullifies the purpose of core decompression and leads to a gradual increase in the intramedullary pressure with subsequent pain. Progressive severe pain leads to clinical failure necessitating total hip replacement whereas the presence of the tantalum metallic implant complicates subsequent surgical procedures including total hip replacement.

SUMMARY OF THE INVENTION

The present invention advances the art and provides technology for treating early stage ONH when the femoral head is still round and therefore salvageable. After removing the necrotic tissue, a mechanically- and biologically-sound biodegradable template is used for reconstitution of the osteonecrotic area within the femoral head.

In this invention, we developed a mechanically robust and functionally-graded scaffold (FGS) with spatiotemporally-controlled degradation and mechanical to properties as a filler for the core decompression tunnel. The FGS for ONH treatment was composed of three sections/segments of spatially-graded porosity: a proximal segment to support the subchondral area, a middle (intermediary) section/segment located in the main osteonecrotic area of the femoral head, and a distal section/segment to support the cortical-like structure (FIG. 1).

The proximal and distal segments of the scaffold were designed relatively less porous to mimic cortical bone, and provide support to withstand compressive mechanical loads and maintain the integrity of the articular surface. The middle segment was designated to possess relatively higher porosity to mimic the trabecular bone of the femoral head, which provides an appropriate template for vascularization and new bone ingrowth and mechanical stability against bending moments applied to the femoral head. In one embodiment, we utilized additive manufacturing (AM) technology to form FGSs with controlled porosity for various segments of the FGSs in a single-stop-shopping process. AM technology also enables the customization of FGS for individual patients based on the anatomical size and level of ONH condition. Biodegradable poly($\varepsilon$-caprolactone) (PCL) and $\beta$-tricalcium phosphate ($\beta$-TCP) were used for the fabrication of FGS because PCL and $\beta$-TCP are in current clinical use and can provide an appropriate scaffold for bone tissue engineering. We first characterized the physical and mechanical properties of each segments of FGS. A comprehensive animal study was conducted to show the potential of design and material of FGS for promoting bone ingrowth and regeneration in core decompression bone tunnel of rabbit femoral heads to mimic treatment of ONH at early stages.

In one embodiment, an engineered medical device for treatment of osteonecrosis is provided. The device is a cylindrically-shaped biodegradable scaffold made of filaments distinguishing three sections of spatially graded chemical composition, porosity and mechanical strength. The three sections define (1) a proximal section, (2) a distal section and (3) an intermediary section in between the proximal and distal sections. The intermediary section is longer than each of the proximal and distal sections. The proximal and distal sections have a porosity that is less than the porosity of the intermediary section. The proximal and distal sections have a mechanical strength that is higher than the mechanical strength of the intermediary section.

In one example, the proximal section has a porosity that is less than the porosity of the distal section.

In another example, the proximal section has a mechanical strength that is less than the mechanical strength of the distal section.

In still another example, the scaffold is a made of a polymer and a ceramic. The scaffold is made of polycaprolactone (PCL), calcium phosphate, beta-tricalcium phosphate (beta-TCP), hydroxyapatite, or a combination thereof. The three sections could include calcium phosphate or beta-tricalcium phosphate and with that the proximal and distal sections could have a higher calcium phosphate or beta-tricalcium phosphate concentration than the intermediary section resulting in the mechanical strength difference, an osteoconductivity difference, and/or a degradation difference between proximal and distal sections compared to the intermediary section.

In still another example, the mechanical strength difference results from the difference in the porosity between proximal and distal sections compared to the intermediary section.

In still another example, the mechanical strength for the sections varies in a range of 0.5 to 6 MPa, with a stiffness for the sections varying in a range of 20 to 100 Mpa, while preserving that the mechanical strength of the proximal and distal sections is higher than the mechanical strength of the intermediary section.

In still another example, the porosity difference changes gradually from the proximal section to the intermediary section and to the distal section, while preserving that the porosity of the proximal and distal sections is less than the porosity of the intermediary section.

In still another example, the mechanical strength difference changes gradually from the proximal section to the intermediary section and to the distal section, while preserving that the mechanical strength of the proximal and distal sections is higher than the mechanical strength of the intermediary section. In still another example, the porosity of the proximal and distal section is defined between 0% to 40% and wherein the porosity of the intermediary section is defined above 40% to 95%. Alternatively, the porosity of the proximal and distal section is defined between 0% to 30% and wherein the porosity of the intermediary section is defined above 30% to 95%.

In still another example, the scaffold has a biodegradation rate that matches bone regeneration, wherein the biodegradation rate can be tailored specifically to a patient's needs. Alternatively, the three sections each have a biodegradation rate that matches bone regeneration intended and designed for its respective sections.

In still another example, the medical device is adapted to fit in a tunnel bored in a femoral head intended for reconstruction of an osteonecrotic area.

In still another example, one or more growth factors or cellular components are added to the surface of the scaffold.

In still another example, the scaffold is a three-dimensionally printed scaffold. In still another example, the proximal and distal sections mimic cortical bone. In another example, the proximal section mimics a subcondoral surface profile, and/or in another example, the intermediary section is intended to replace trabecular bone of necrotic tissue. In one example, the intermediary section is a template for vascularization and bone ingrowth.

In yet another example, the size, porosity and ceramic content of the device is personalized based on an individual patient's anatomical and physiological condition. A skilled artisan could envision embodiments of a scaffold including more than three sections or segments based on the same approach and philosophy as discussed herein for a scaffold with three segments.

The FGS offers advantages over existing technologies. First, such a synthetic graft prototype of FGS seamlessly integrates both mechanical and biological strategies by mimicry of anatomically-relevant cortical and cancellous segments, in which the cortical segments of the FGS can sustain mechanical loading, and the cancellous segment of the FGS can promote bone ingrowth, osteogenesis and angiogenesis. In addition, the open pore structure and bioresorbable nature of our implants will have an improved integration capability compared to fibular autograft, and porous non-resorbable tantalum implants because both of the currently available grafts either possess or generate an impermeable cortical bony shell to impair vascular invasion and osseointegration. Second, the combination of the 3D printing and the novel biodegradable biomaterials that are suitable for 3D printing allows us to personalize the implants regarding size, anatomical shape, and more uniquely, properties such as tempo-spatial degradation profiles to better facilitate revitalization of the osteonecrotic area of ONH. Third, the FGS is made of polymer-ceramic composite and can be customized in the operating room by cutting and trimming with surgical instruments to fit the patient's specific defect. This feature renders available to patients either catalog-based off-of-shelf products or customized products. Fourth, the personalizable biodegradable FGS can be readily combined with the clinically available cell therapy to further improve the clinical outcome.

BRIEF DESCRIPTION OF THE DRAWINGS

FIGS. 11A-D show TRAP positive cells in the FGS according to an exemplary embodiment of the invention.

DETAILED DESCRIPTION

Materials and Methods

Figure 1:
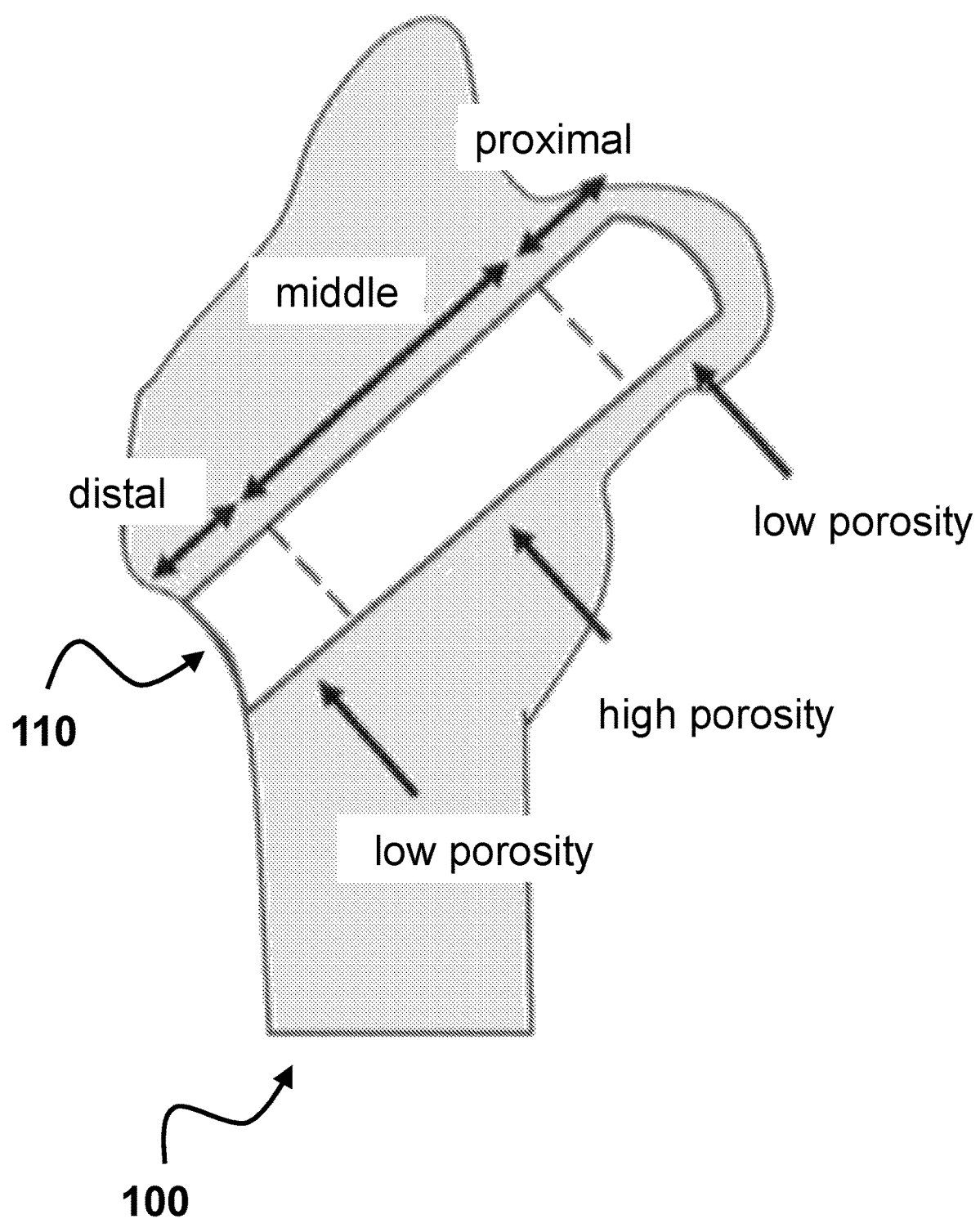
FIG. 1 shows a schematic of the functionally-graded scaffold (FGS) according to an exemplary embodiment of the invention.

Medical-grade poly(ε-caprolactone) (mPCL) pellets (Aldrich Chemical Company) with density of 1.145 g/cm$^3$ (Mn=80,000) were used as received. β-tricalcium phosphate (β-TCP) powder with a specific surface area of 17 m$^2$/g and particle size of mesh 60 was obtained from Nanocerox, Inc. (Ann Arbor, Mich.). A slurry was prepared by dispersing β-TCP powder in acetone at 50° C., followed by gradual incorporation of PCL pellets. A PCL:β-TCP:acetone weight ratio of 80:20:400 was used. Vigorous mechanical stirring was performed for 3 h to ensure the homogenous distribution of the β-TCP particles in the PCL slurry. The slurry was poured out evenly into glass plates, left overnight to evaporate, and further dried in a vacuum overnight to remove any residual acetone. Then, as raw material for AM process, the material was shaped as long filaments via warming up and extruding through a 2.2-mm orifice of an in-house-made filament-maker machine.

Design and Fabrication of PCL-β-TCP FGS

FGS for ONH treatment was designed to be composed of three segments of spatially-graded porosity, including 3.5 mm in diameter×4 mm in length for proximal segment of 15% porosity, 3.5 mm in diameter×17 mm in length for middle segment and 3.5 mm in diameter×6 mm for distal segment of FGS. Such a graded scaffold was formed in one piece using our in-house-built layer-by-layer 3D fabrication system, Hybprinter. Briefly, the filaments were fed into the machine AM machine where they were melted at 140° C., extruded as 350 μm struts and laid down in 0/90° patterns layer-upon-layer to form porous lattice-shaped scaffolds. The layer thickness (=distance between the sequential layers) was selected equal to 300 μm. The spacing between the adjacent struts was defined in a way to provide 15% porosity in proximal segment and distal regions and 60% porosity in middle region. Also, similar setting was used to form samples for physical and mechanical characterizations. All scaffolds were surface-treated in 5M NaOH for 12 h at room temperature to enhance their hydrophilicity and microroughness on the strut surface.

Physical Characterizations

Porosity

Porosity of samples for proximal, middle, and distal segments was measured using high-resolution micro-CT scanner (SMX-100CT-SV3; Shimadzu Co., Kyoto, Japan). The entire set of radiographs was deconvoluted by computer software to reconstruct a 3D image of the microstructure with a voxel size of 12 μm$^3$. The 3D data were processed with commercially available 3D image processing software (VG Studio MAX 2.0; Volume Graphics, Heidelberg, Germany), and the porosity of each segment of the scaffold was measured from the binary material images. The spatial boundary between the pores and the scaffold was determined based on the remarkable difference of their intensities.

Scanning Electron Microscopy

AM-made scaffolds were also scanned via secondary electron emission imaging using SEM (FEI XL30 Sirion) to analyze strut size, pore size, and layer thickness as well as to observe surface morphology of the struts. Three samples per group were used. The PCL-β-TCP scaffolds were first sputter-coated with gold (10 nm) (SPI Sputter, SPI Supplier Division of Structure Prob Inc., West Chester, Pa., USA) to make them electrically conductive. The SEM acceleration voltage was set to 5 kV.

Water-Uptake

The water-uptake characteristic represents hydrophilicity of the scaffolds and the surface condition of the scaffold struts for cell anchorage, adhesion and proliferation as well as new tissue ingrowth and integration. The water uptake ability of the porous scaffolds was determined by completely immersing the samples in distilled water for 60 s. The bulk water accumulated on the outer surfaces of the samples was removed via blotting with a piece of wet filter paper. Then, the wet scaffolds were weighed immediately using an electronic balance (XS105, METTLER TOLEDO, Columbus, Ohio). The percentage of water uptake was determined as $$WaterUptake\ \% = \frac{W_w - W_d}{W_d} \times 100$$

where $W_w$ and $W_d$ are the weight of wet and dry samples, respectively. The test was conducted using five specimens of each sample type (i.e., different strut size). Each measurement was triplicated for each scaffold and the average value was calculated. Five samples per group were tested.

Degradation

The degradation of PCL-β-TCP scaffolds with 15% and 60% porosity was compared in alkaline medium. To accelerate the hydrolysis reaction 5M Sodium hydroxide (NaOH) was used. Scaffolds of 5×5×10 mm$^3$ were submerged in 2 mL of NaOH at 37 degrees Celsius. The PCL scaffolds were dried and weighted after 12 hr, 24 hr, 36 hr and 48 hr. The degradation rate was determined as weight loss percentage at each time point.

Mechanical Characterization

Compression Test

The mechanical properties of the scaffolds were measured using an Instron 5944 uniaxial testing system with a 2 kN load-cell (Instron Corporation, Norwood, Mass.). Specimens with 5×5 mm$^2$ square cross-section and 10 mm in height were mechanically tested under compression between two platens (one self-aligning, one fixed) at a speed of 0.1% strain/sec up to 25% strain with 1 N preload. Displacement was determined from an extensometer (Epsilon Technology Corp, Jackson Wyo.) attached to the two platens. Five samples were tested for each group of 15% and 60% porosity. The testing protocol was adapted from the reference (22) where, for all the specimens, the apparent modulus of elasticity was calculated as the slope of the initial linear portion of the stress-strain curve. The effective stress values were determined as the compressive loading value per the apparent initial cross-sectional area of each test specimen. The strain values were calculated via dividing the deformation values with the initial specimen height. Yield compression strength was defined as the intersection of the stress-strain curve with a line with a slope equal to the modulus starting at an offset of 1% strain. Five samples per group were measured.

Flexural Test

To measure bending flexural stiffness of scaffolds, 3.7 mm×3.9 mm×70 mm samples of 15% and 60% porosity were tested under 3-point bending following ASTM D790 instructions. Bending tests were conducted using a support span of 56 mm, which resulted in a support span to specimen depth ratio of 16:1 (depth=3.5 mm). A 100 N load sensor was used for the test. Following application of a 0.1 N preload, the central loading nose was lowered at a rate of 0.1% strain/sec to 5% strain. The apparent flexural modulus was calculated as the slope of the initial linear portion of the stress-strain curve (between 0.1 and 1.1% strain). Five samples per group were measured.

In Vivo Evaluation

Animals

Five male New Zealand White rabbits (Charles River Laboratories Inc. USA) weighing from 3.5 to 4.0 kg were used in this study. For operative procedure, animals were anesthetized by administration of 40 mg/kg ketamine and 4 mg/kg xylazine. Additional inhalation anesthesia was performed with isoflurane. Analgesia was administered by injection of 0.5 mg/kg buprenorphine twice a day for the first 2 days after surgery. All experiments with animals were performed following Stanford University Animal Care and Use Committee guidelines. All research animals has been approved by Stanford APLAC #28999, following approved guidelines by the Stanford University's Institutional Review Board.

Surgical Procedure

A lateral skin incision was created to expose the greater trochanter. Core decompression of 3.5 mm diameter was performed from distal end of the greater trochanter along the axis of the femoral neck on both hips. The tunnel direction was in the mid axis of the femoral neck. First, a bone tunnel was created from laterally towards the femoral head superomedially using a 2 mm diameter drill under fluoroscopic guidance. The depth of bone tunnel was approximately 27 mm. This 2 mm tunnel was widened with a 3.5 mm diameter drill bit. FGS (3.5 mm in diameter and 27 mm in length) was randomly assigned and inserted into the tunnel in the right or the left hip and the other tunnel was kept empty as a control. The scaffold was press fitted into the bone tunnel. Five implants were used for this study based on our previous experience where bone tunnel was created on the rabbit femur. Power analysis indicated that a sample size of five per group would provide 80% statistical power to detect significant differences between the groups ($\alpha$=0.05, $\beta$=0.20) using analysis of variance (ANOVA).

Micro-CT Analysis

A microfocus X-ray computed tomography system (SMX-100CT-SV3; Shimadzu Co., Kyoto, Japan) was used to acquire microstructural information for proximal femur at 8 weeks after implantation of FGSs. The entire set of radiographs was deconvoluted by computer software to reconstruct a 3D image of the microstructure with a voxel size of 12 μm and was evaluated using 3D image-processing software VG studio MAX 2.0 (Volume Graphics, Heidelberg, Germany). A cylindrical region of interest (3.5 mm in diameter×4 mm in length for proximal segment, 17 mm in length for middle segment and 6 mm for distal segment of FGS) was co-centrically positioned over the core decompression site. The location of original bone tunnel in empty-tunnel group was confirmed on CT image based on to anterior-posterior and lateral view of X-ray taken during surgery. The volume of new bone and remaining FGS was determined by the software. Thresholds were applied to differentiate between new bone and residual scaffold material in the region of interest.

Histology

After 8 weeks of implantation, following the euthanasia, the proximal femoral bone was harvested and prepared for histology. Three samples from each group were prepared for decalcified histological analysis. The specimens were fixed in 10% phosphate-buffered formaldehyde (pH 7.25) for 24 h and decalcified in 15% EDTA (pH 8.0) at 4° C. Complete decalcification was confirmed by X-ray. Then, the samples were dehydrated in graded ethanol (70, 85, 90 and 100%), then cleared in xylene, and embedded in paraffin. Thin sections (8 μm) were cut and mounted on glass slides. Before staining, the sections were deparaffinized in 100% xylene and rehydrated in graded ethanol. Specimens were analyzed by hematoxylin and eosin (H&E) staining and tartrate resistant acid phosphate (TRAP) staining. The number of TRAP positive multinucleated cell was counted. Two samples from each group were prepared for undecalcified histology. The specimens were dehydrated in graded ethanol after fixed in 10% formaldehyde, and then embedded in a cold setting epoxy resin. Thick specimens (250 μm) were cut with a band saw, and ground to a thickness of 50 μm. Each section was evaluated with Stevenel's blue and Van Gieson's picrofuchsin staining. TRAP staining was also performed.

Statistical Analysis

All data are expressed as means±standard deviation (SD). For the comparison among three segments (proximal, middle and distal), the homogeneity of the variance among groups was assessed with the Bartlett test before examined with ANOVA. When the variance was homogeneous, comparisons between groups were performed with one-way ANOVA followed by a post hoc test (Tukey-Kramer multiple comparison test). All analyses were performed using JMP 9 (SAS Institute, Cary, N.C.). For comparison between two groups (empty group vs. scaffold group and low porosity segment vs. high porosity segment), Student's t test was used to investigate the significant difference between the groups. Values of p<0.05 were considered statistically significant.

Results

Morphology of FGS

Figure 2:
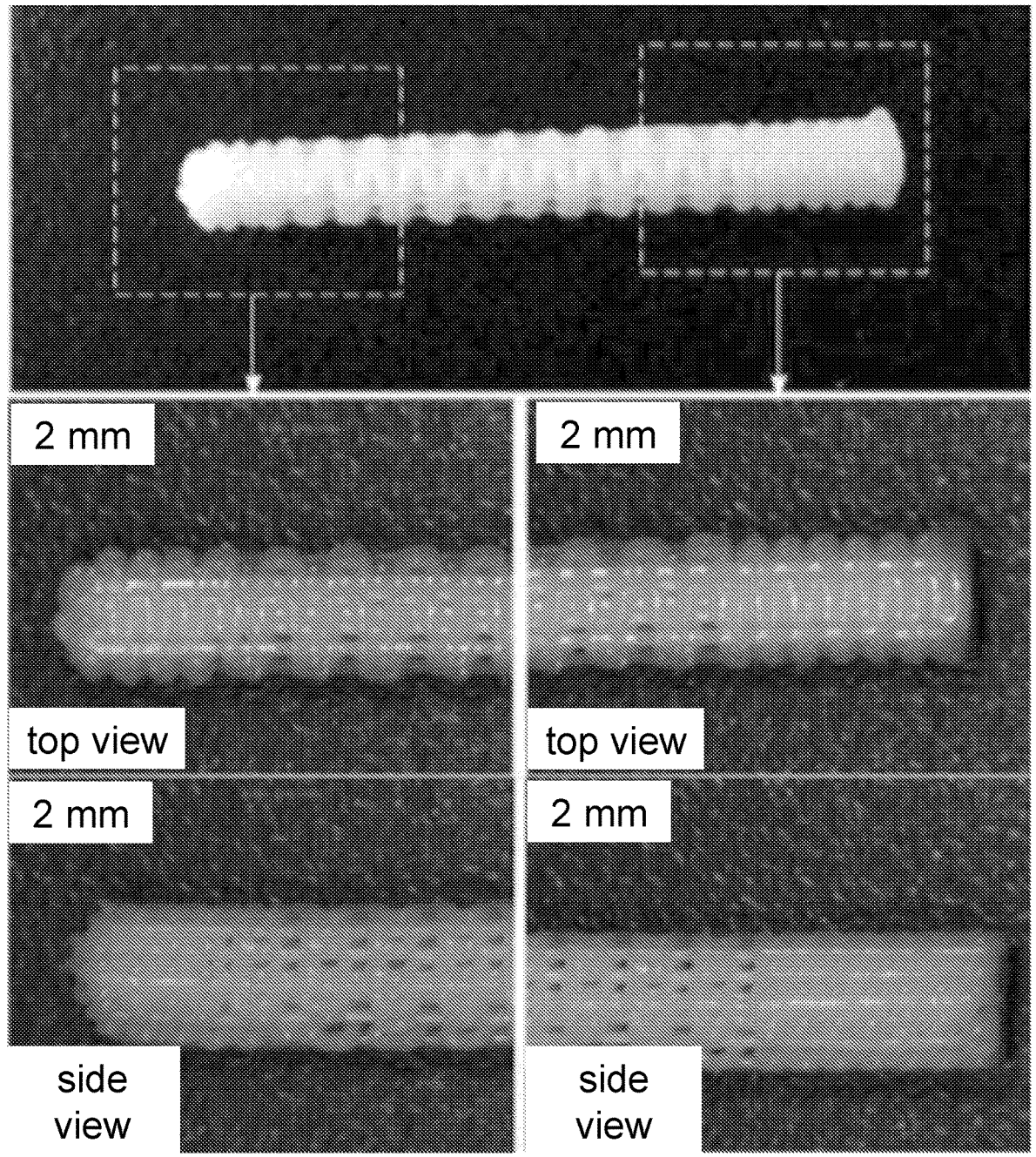
FIG. 2 shows digital photos of a representative FGS according to an exemplary embodiment of the invention.
Figure 3:
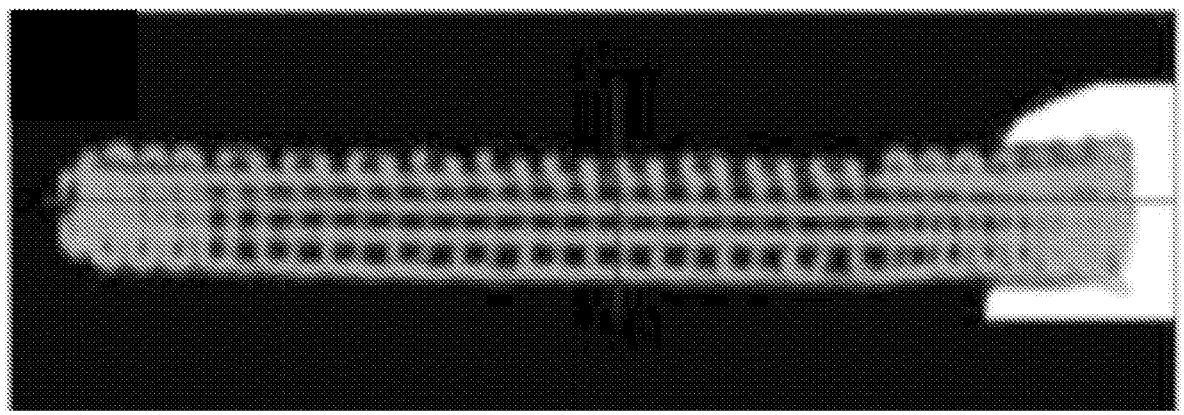
FIG. 3 shows a representative micro CT image of a longitudinal cross-section of FGS according to an exemplary embodiment of the invention.
Figure 4:
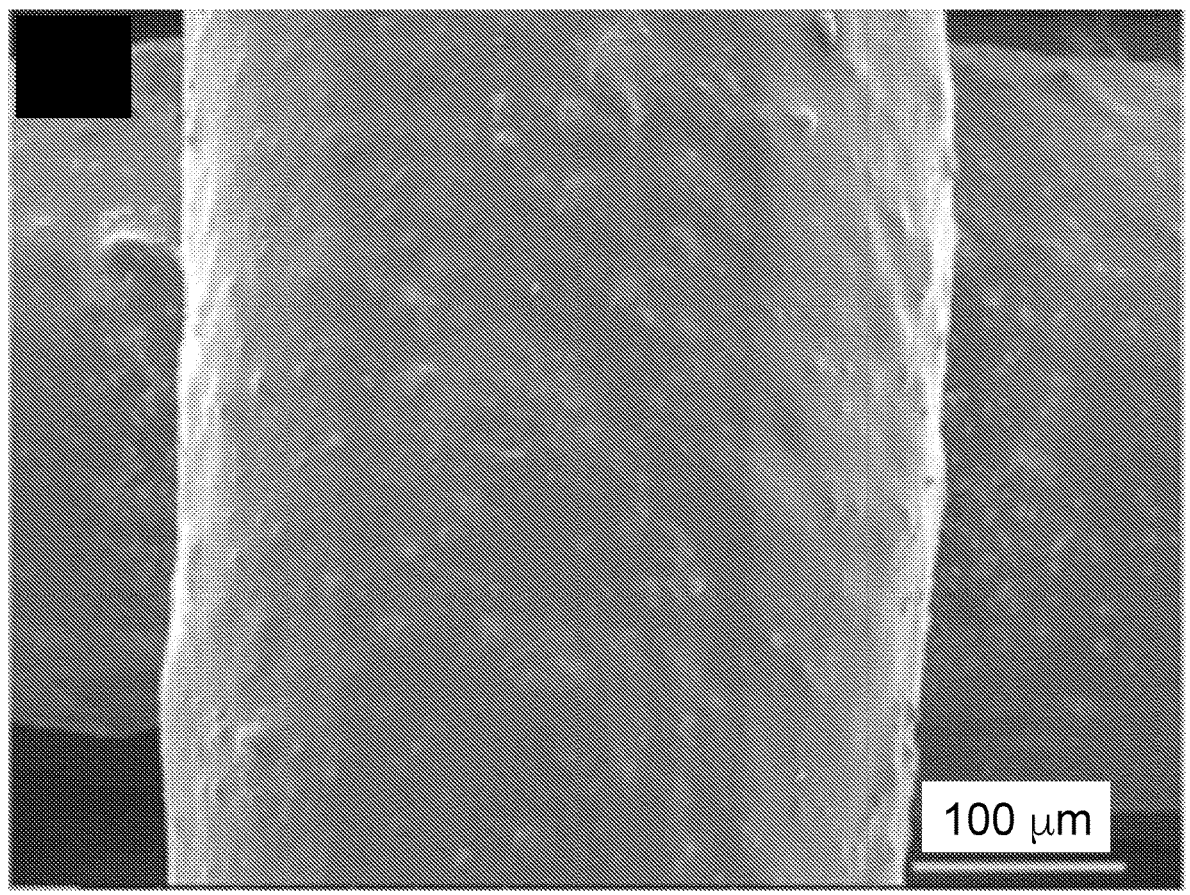
FIG. 4 shows SEM image of scaffold strut surface according to an exemplary embodiment of the invention.
Figure 5:
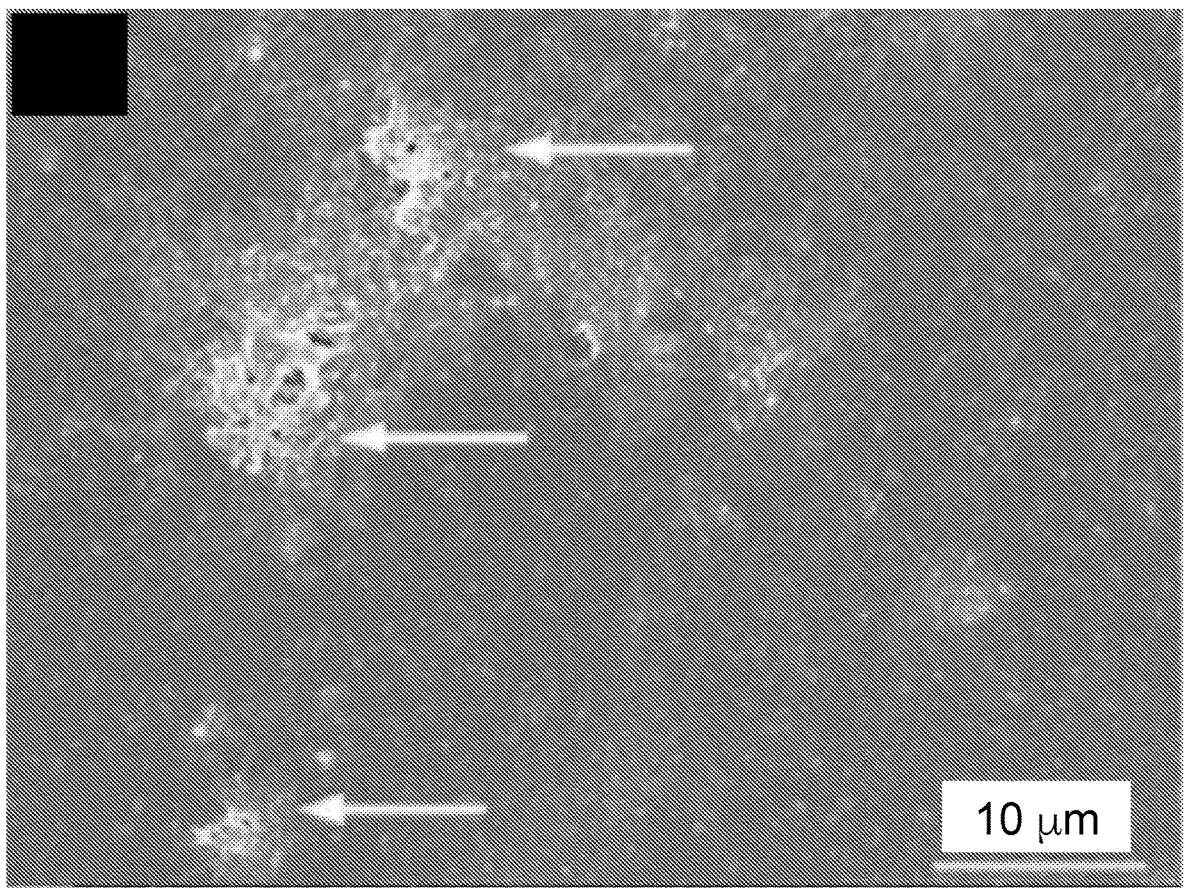
FIG. 5 shows SEM image of scaffold strut surface after NaOH treatment according to an exemplary embodiment of the invention.

FIG. 2 show digital photos of a representative FGS. The proximal and distal less porous segments are shown from both top and side views. FIG. 3 shows a representative micro CT image of a longitudinal cross-section of FGS. These images confirmed the successful fabrication of a FGS with two less porous segments in the two ends and a more porous middle segment. Also, the SEM image of scaffold strut surface is shown in FIGS. 4 and 5, demonstrating roughness (FIG. 4) and micro-pores (FIG. 5) formed after NaOH treatment.

Porosity and Water-Uptake

Figure 6A:
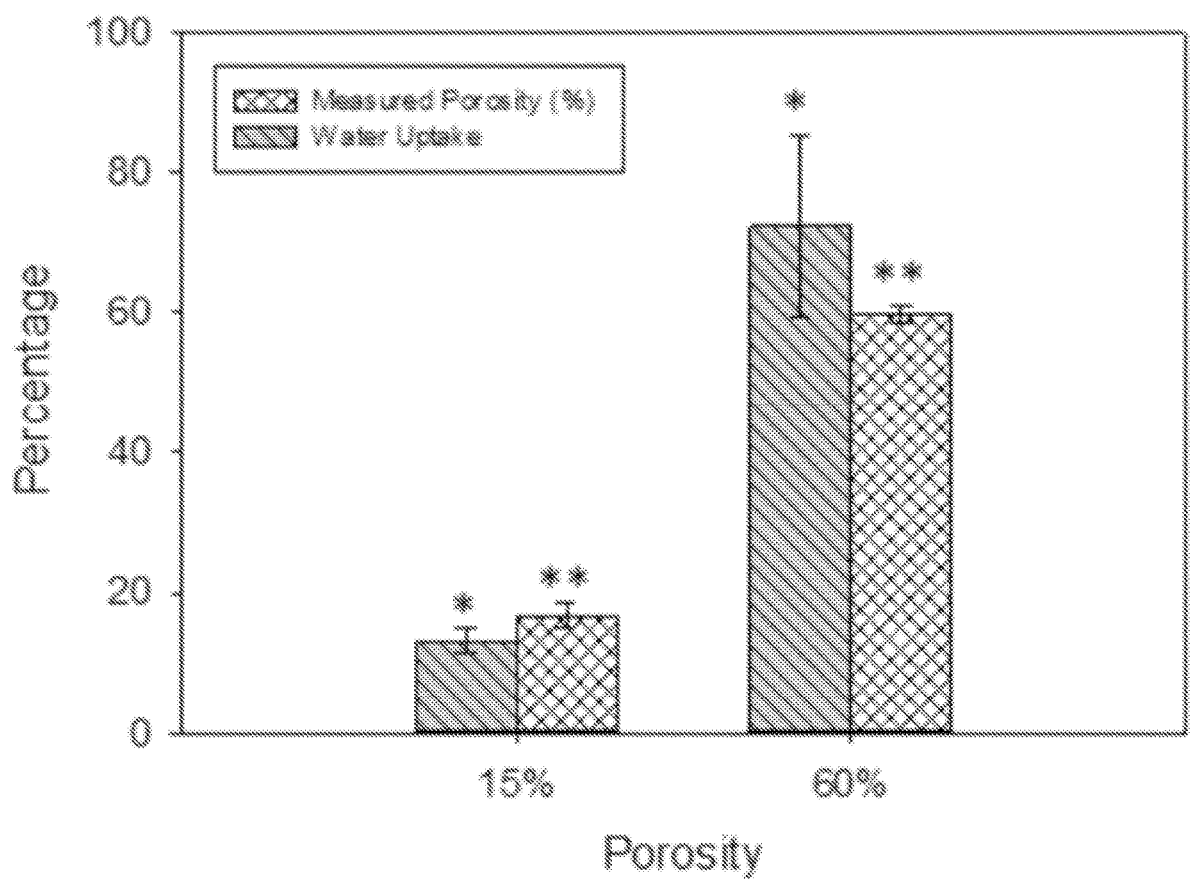
FIGS. 6A-C show physical characterization of a scaffold according to an exemplary embodiment of the invention.

FIG. 6A shows the porosity and water-uptake of scaffolds for high and low porosity segments of FGS construct. The porosities of scaffolds via micro CT analysis were 16.8±1.8%, 59.5±1.2% and 16.4±1.7% for proximal, middle and end segment, respectively, which were in good agreement (~2.0% difference) with designed porosity. Water-uptake yielded values of 15.1±2.1% for dense segments and 72.3±12.9% for the less dense segment, respectively. There was no significant difference in water-uptake and porosity measurements, demonstrating excellent hydrophilicity of sample surface treated by alkali.

Degradation

Figure 6B:
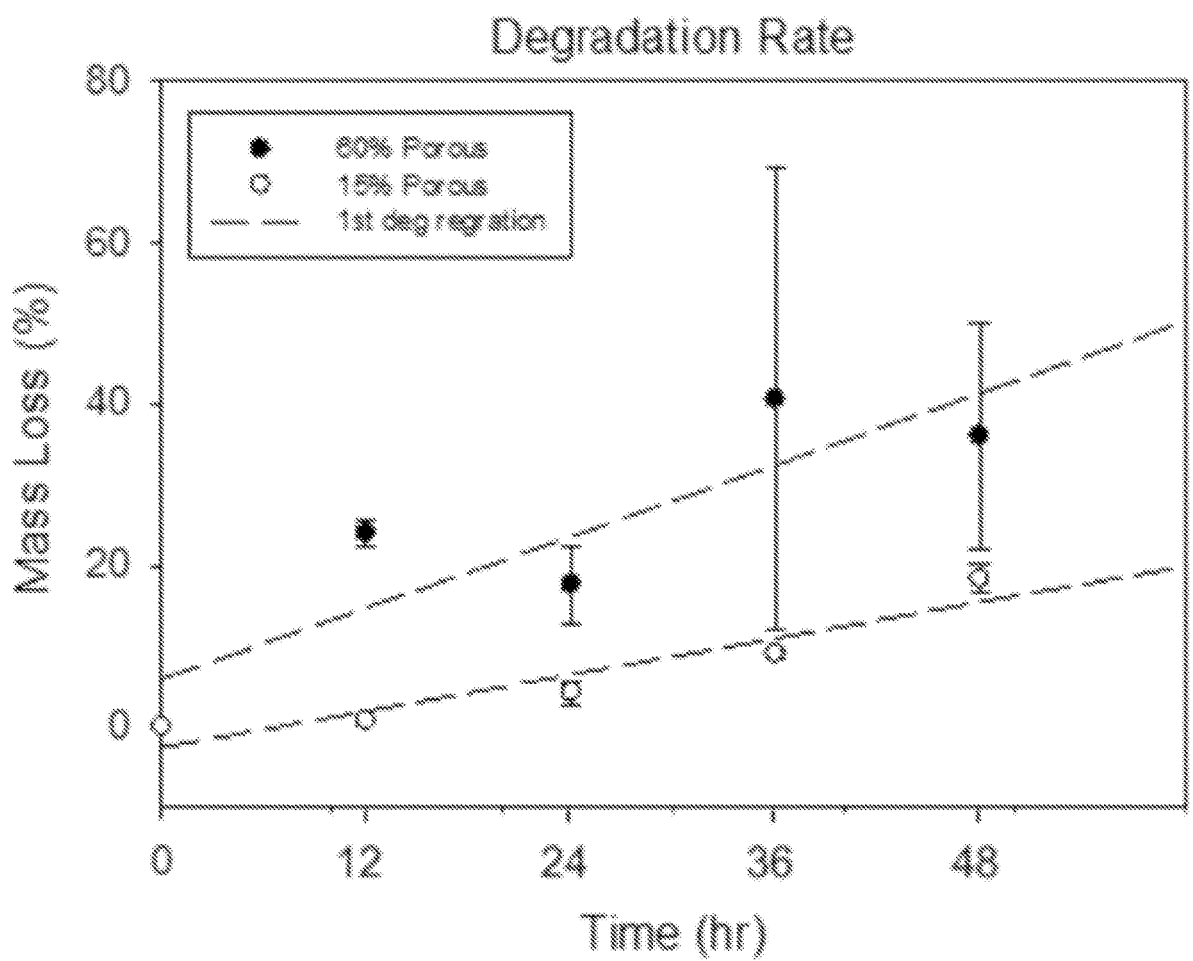
Figure 6C:
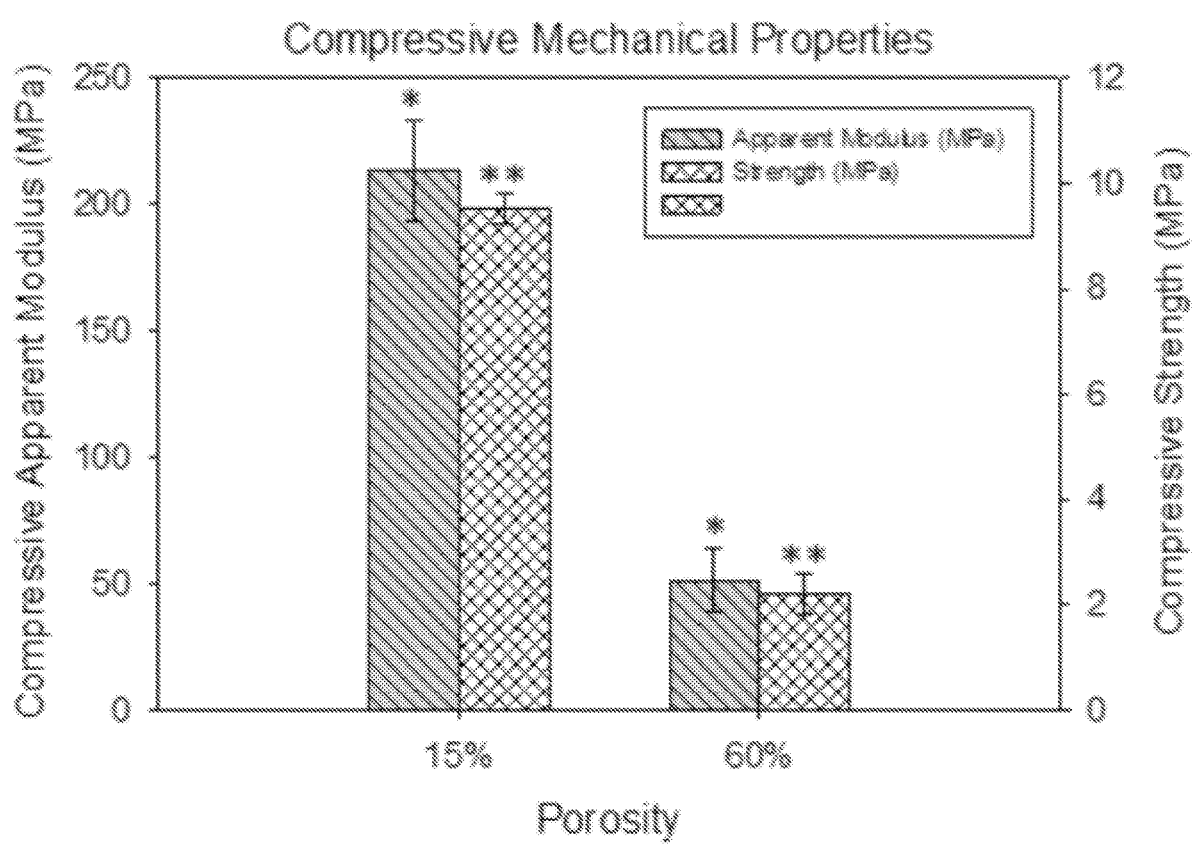

FIG. 6B shows the accelerated degradation rates of scaffolds of high and low porosity in alkaline medium (5M NaOH) for every 12 hr up to 48 hr. Both scaffolds exhibited almost linear degradation rates, and the scaffolds of 60% porosity demonstrated significantly higher weight loss rate in vitro compared to those of lower porosity under such an accelerated degradation condition.

Mechanical Properties

The strength and apparent modulus of elasticity of PCL-β-TCP scaffolds with low and high porosity were measured under compression. As shown in FIG. 2C, the strength of the 60% porous scaffold was 2.2 MPa in average which is comparable with the strength of human trabecular bone (ranging from 0.2 to 10 MPa). The apparent modulus of 60% porous scaffolds was about 51.5 MPa. The scaffolds with lower porosity exhibited significantly higher compressive strength and apparent elastic modulus: 9.5 MPa and 213.4 MPa, respectively. Also, flexural mechanical stiffness of the 60% porous scaffolds under three point bending condition was measured equal to 104.8±19.7 MPa.

Gross Inspections

All rabbits tolerated the operation well. No infection of the operation site or migration of the implant was seen in dissection after euthanasia. No apparent adverse reactions including inflammation or foreign body reactions were observed around implants.

Micro CT Analysis

Figure 7A:
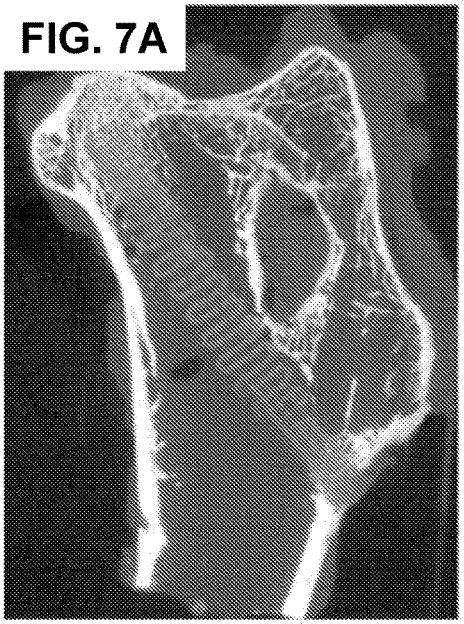
FIGS. 7A-D show microCT images of rabbit femoral heads in the presence and absence of FGS at 8 weeks after core decompression according to an exemplary embodiment of the invention.
Figure 7B:
Figure 7C:
Figure 7D:
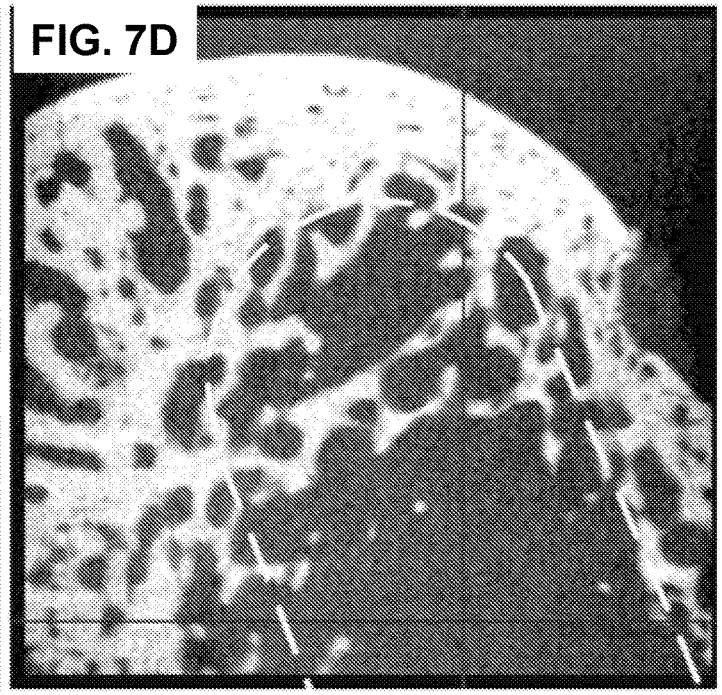

Micro CT was used to measure the volumes of residue FGS and newly formed bone of explants at 8 weeks after surgery. FIGS. 7A-D show representative micro CT images of explants with and without FGS. The CT images showed that the lattice pattern and structural integrity of the scaffold were well maintained at 8 weeks after implantation. In the FGS group, the mineralized tissue was observed in the center of FGS in femoral head (FIG. 7B). In the empty-tunnel group, most of the space in the bone tunnel remained empty, but there was some mineralized tissue around the tip of the tunnel (FIG. 7D).

Figure 8A:
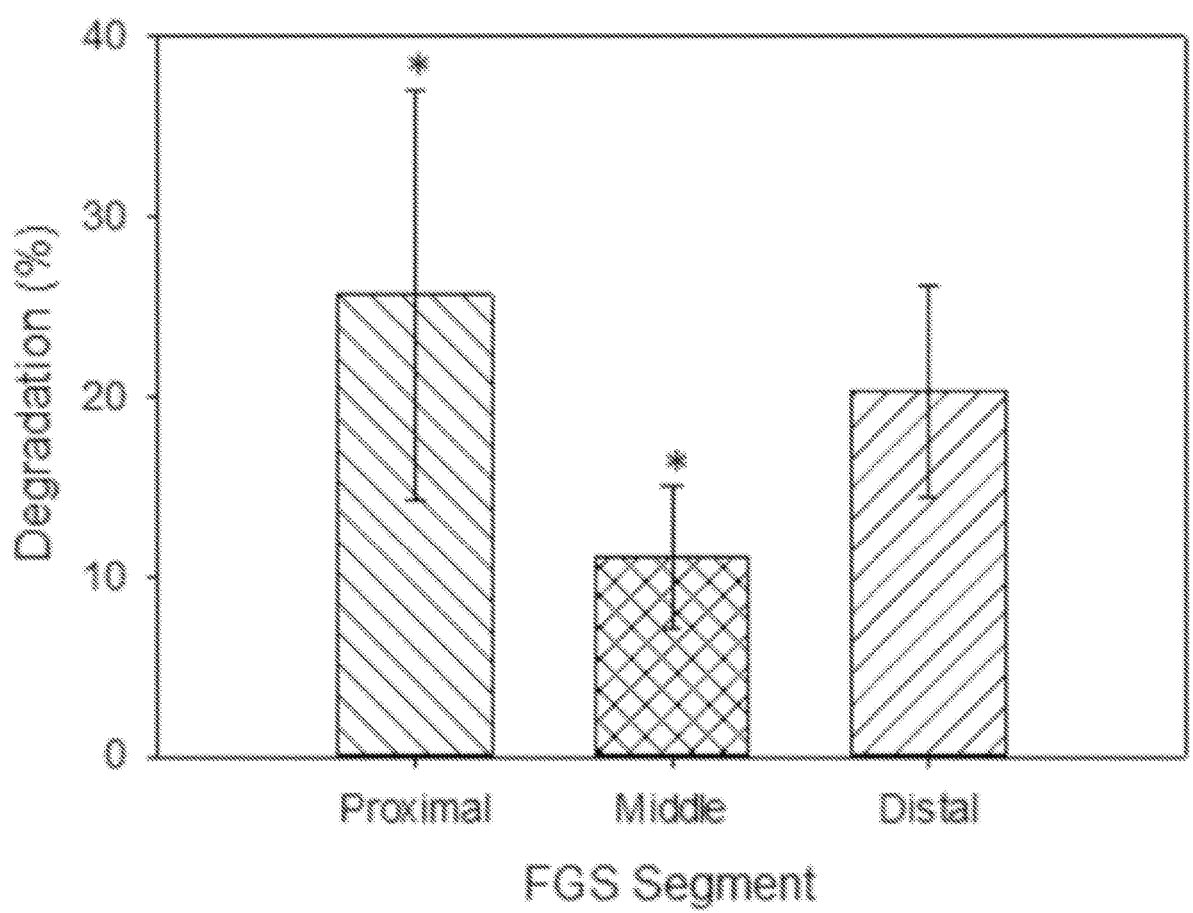
FIGS. 8A-C show quantitative analysis of scaffold degradation and bone ingrowth in the FGS at 8 weeks after implantation according to an exemplary embodiment of the invention.

FIG. 8A shows the degradation rate of the FGS that was quantified using CT analysis. The degradation rates of proximal, middle and distal segments were 25.7±11.3%, 11.1±4.0%, and 20.4±6.9%, respectively. The difference in degradation rate between proximal and middle segments was statistically significant (p=0.028), whereas the differences in degradation rate between proximal and distal segments, or between middle and distal segments were not (p=0.539 and 0.180, respectively).

Figure 8B:
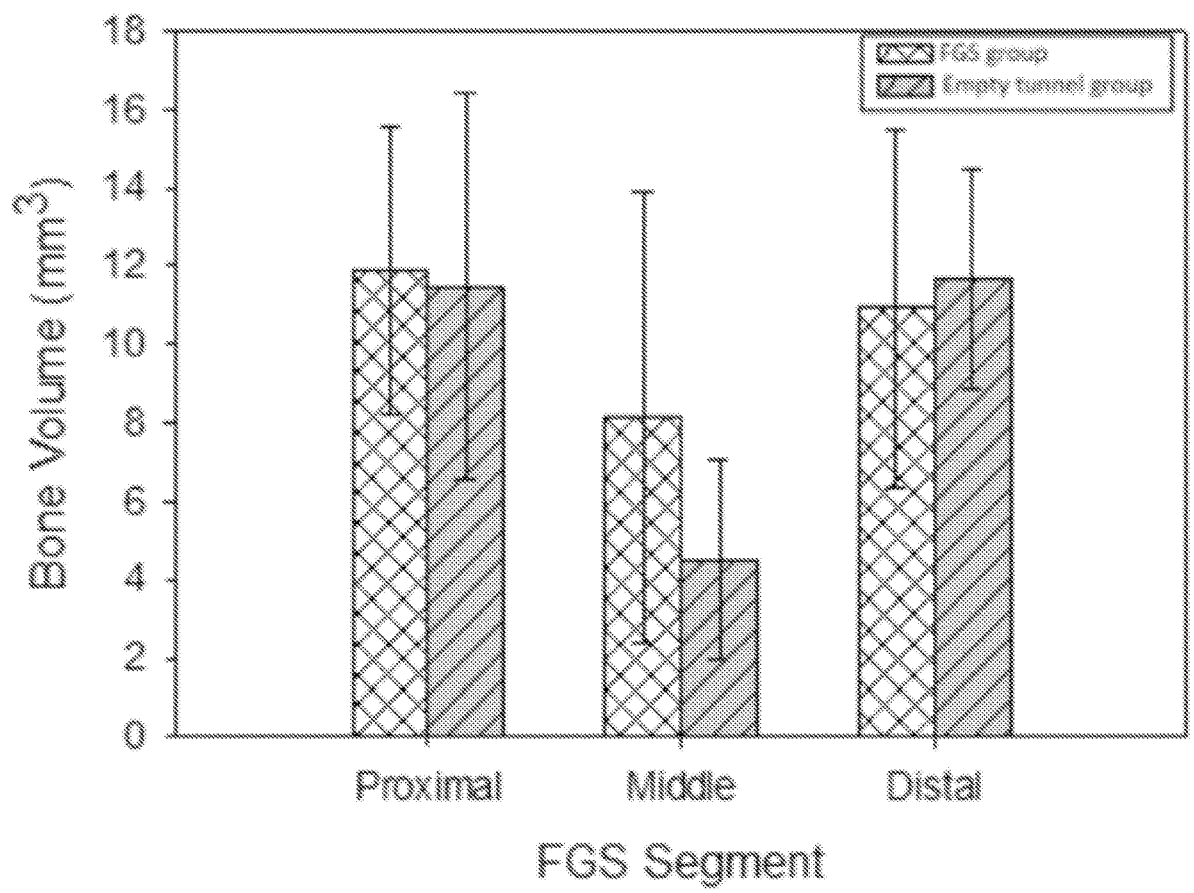
Figure 8C:
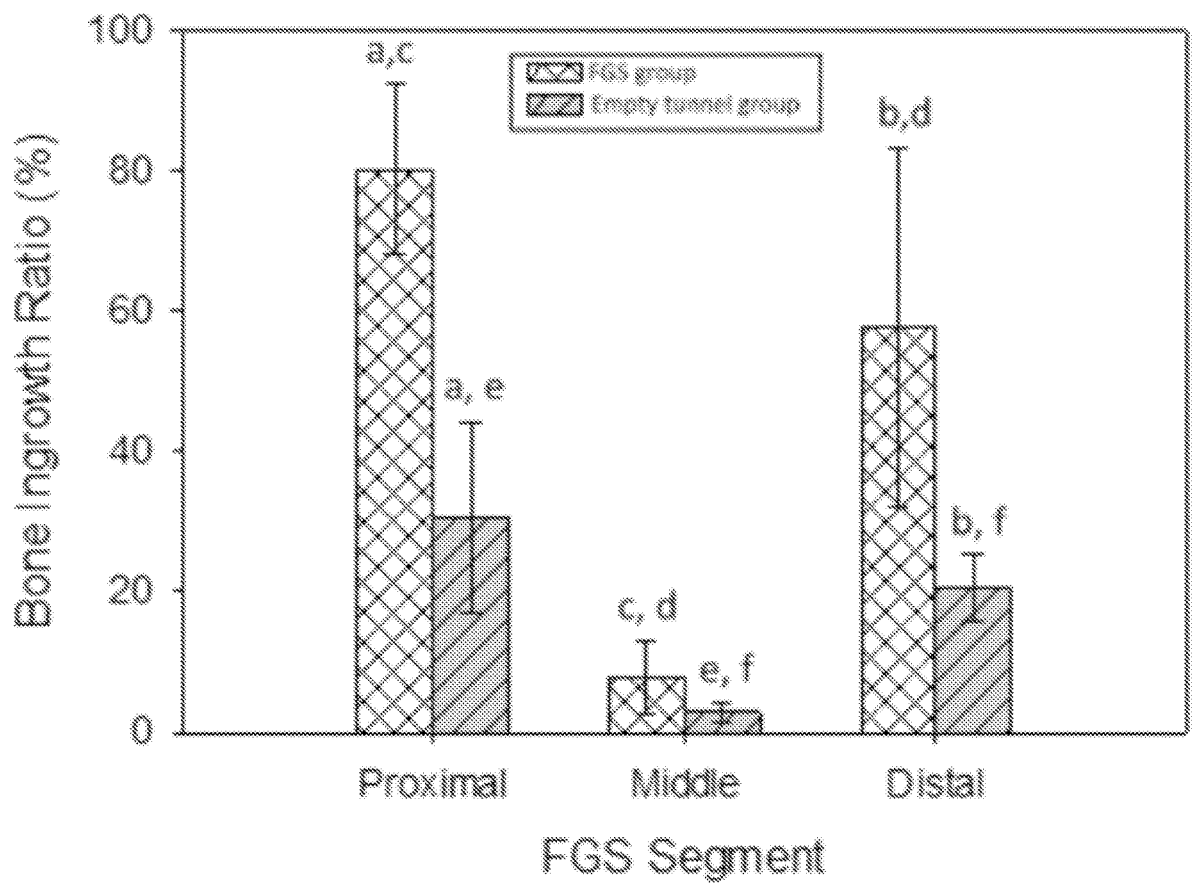

The volumes of newly formed bone measured at 8 weeks post surgery were measured 11.9±3.6 mm$^3$ in the proximal segment, 8.2±5.8 mm$^3$ in the middle segment, 10.9±4.6 mm$^3$ in the distal segment for the scaffold group, and were 11.5±4.9 mm$^3$ for the proximal segment, 4.5±2.6 mm$^3$ for the middle segment and 11.7±2.8 mm$^3$ for the distal segment for the empty group (FIG. 8B). The bone ingrowth ratio for the scaffold group was 80.1±12.1% for the proximal segment, 7.7±5.2% for the middle segment and 57.7±25.4% for the distal segment (FIG. 8C). The bone ingrowth ratio for the empty-tunnel group was 30.5±13.5% for the proximal segment, 2.8±1.6% for the middle segment and 20.5±4.8% for the distal segment. The difference in bone ingrowth ratio between the scaffold-filled group and the empty-tunnel group was statistically significant for the proximal segment (p=0.0053) and distal segment (p=0.031), but not for the middle segment (p=0.164).

Histology

Figure 9A:
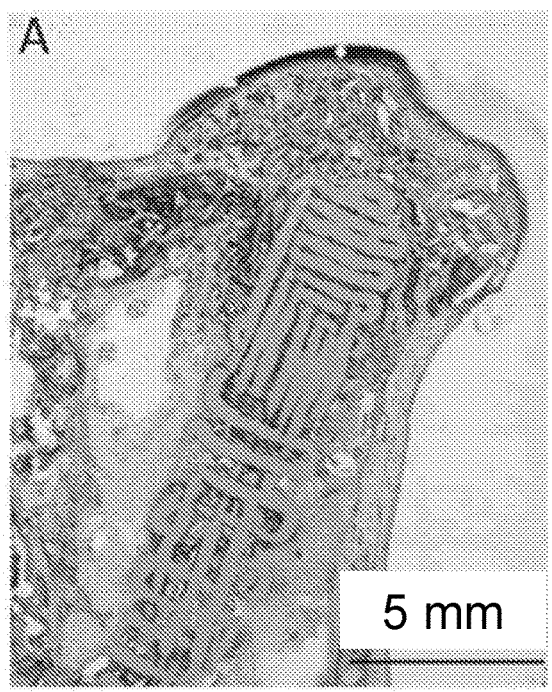
FIGS. 9A-C show bone ingrowth in the FGS in the non-decalcified histology sample according to an exemplary embodiment of the invention.
Figure 9B:
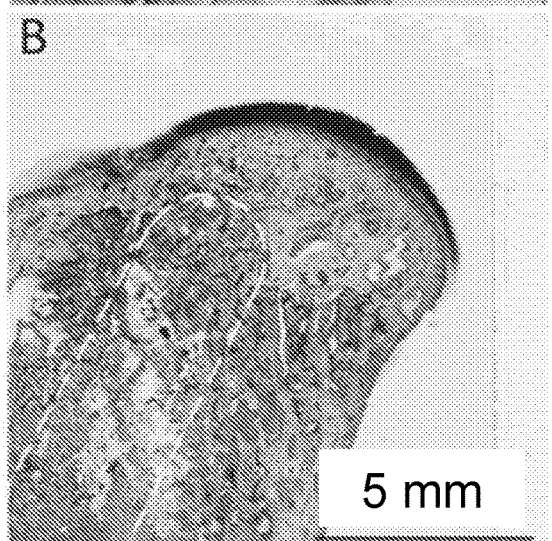
Figure 9C:
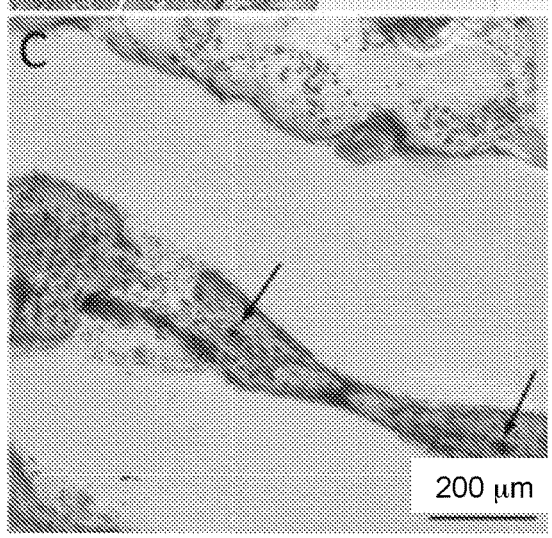
Figure 10A:
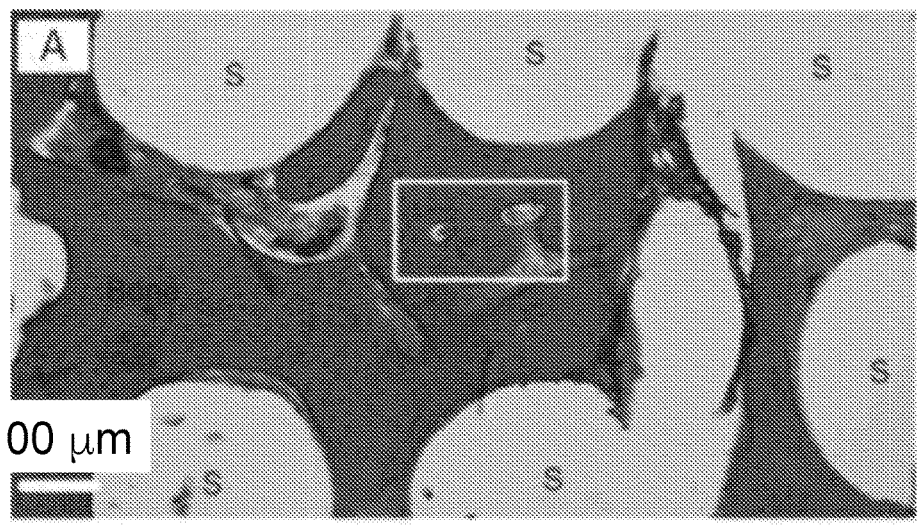
FIGS. 10A-C show bone ingrowth and regeneration in the decalcified histology samples according to an exemplary embodiment of the invention.
Figure 10B:
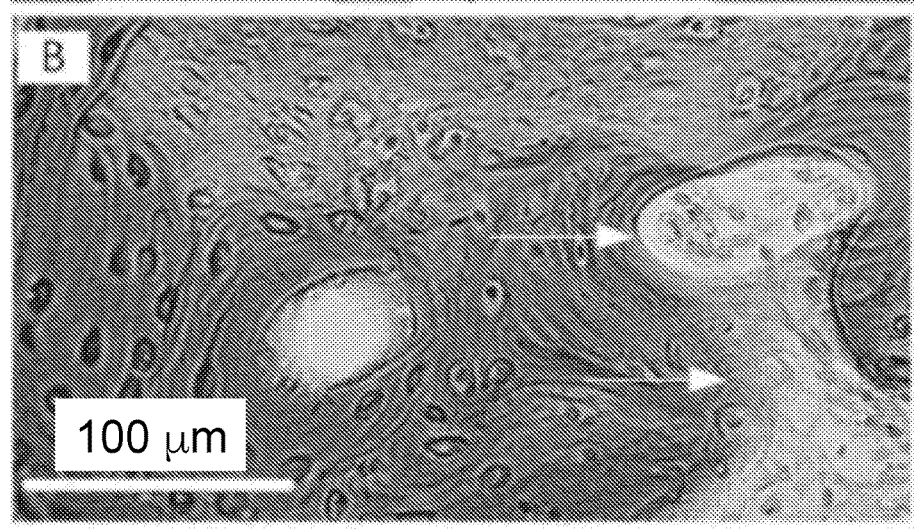
Figure 10C:
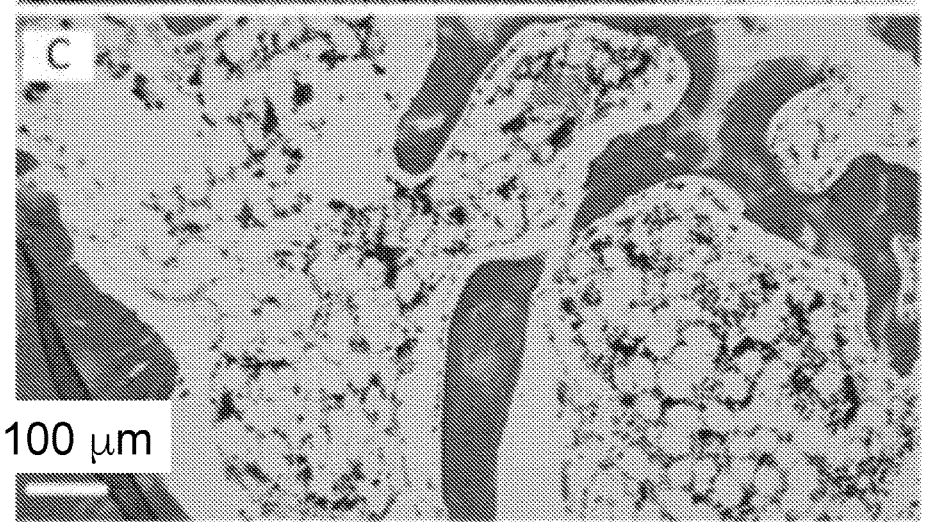

At 8 weeks after implantation, considerable amount of new bone was seen in the undecalcified histology samples of both the FGS group (FIG. 9A) and empty-tunnel groups (FIG. 9B). In the FGS group, the newly formed bone tissue in the porous area of FGS was in direct contact with the scaffold strut (FIG. 9C). The images from paraffin embedded decalcified samples showed that almost all space available was occupied by newly formed bone in proximal segment of FGS (FIG. 10A). At high magnification images, Haversian canal- and Volkmann's canal-like structures were observed containing blood cells even near the center of the FGS (FIG. 10C). The number of TRAP positive cell on the surface of the scaffold was 5.5±1.7 per mm$^2$ in the proximal segment, 3.8±1.8 per mm$^2$ in the middle segment, and 7.1±2.2 per mm$^2$ in the distal segment. The difference in the TRAP positive cell number between the distal segment and middle segments was significant, while the difference between proximal segment and middle segment, and proximal segment and distal segment was not statistically significant (FIGS. 11A-D).

What is claimed is:

1. An engineered medical osteonecrosis treatment device, comprising:
   a cylindrically-shaped biodegradable scaffold made of filaments having three cylindrical sections of spatially graded chemical composition, porosity and mechanical strength, wherein the three cylindrical sections distinguish in cylindrical alignment with each other a proximal cylindrical section, a distal cylindrical section and a single intermediary cylindrical section positioned in between the proximal and distal cylindrical sections,
   wherein the intermediary cylindrical section is longer than each of the proximal and distal cylindrical sections,
   wherein a porosity of the proximal and distal cylindrical sections across the entire proximal and distal cylindrical sections is less than a porosity across the entire intermediary cylindrical section, and
   wherein a mechanical strength across the entire proximal and distal cylindrical sections is higher than a mechanical strength across the entire intermediary cylindrical section.

2. The engineered medical osteonecrosis treatment device as set forth in claim 1, wherein the proximal cylindrical section has a porosity which is less than the porosity of the distal cylindrical section.

3. The engineered medical osteonecrosis treatment device as set forth in claim 1, wherein the proximal cylindrical section has a mechanical strength which is less than the mechanical strength of the distal cylindrical section.

4. The engineered medical osteonecrosis treatment device as set forth in claim 1, wherein the scaffold is a made of a polymer and a ceramic.

5. The engineered medical osteonecrosis treatment device as set forth in claim 1, wherein the scaffold is made of polycaprolactone (PCL), calcium phosphate, beta-tricalcium phosphate (beta-TCP), hydroxyapatite, or a combination thereof.

6. The engineered medical osteonecrosis treatment device as set forth in claim 1, wherein the three cylindrical sections comprise calcium phosphate or beta-tricalcium phosphate and wherein the proximal and distal cylindrical sections have a higher calcium phosphate or beta-tricalcium phosphate concentration than the intermediary cylindrical section resulting in (i) the mechanical strength difference, (ii) an osteoconductivity difference, (iii) a degradation difference between proximal and distal cylindrical sections compared to the intermediary cylindrical section, or a combination thereof.

7. The engineered medical osteonecrosis treatment device as set forth in claim 1, wherein the mechanical strength difference results from the difference in the porosity between proximal and distal cylindrical sections compared to the intermediary cylindrical section.

8. The engineered medical osteonecrosis treatment device as set forth in claim 1, wherein the mechanical strength for the cylindrical sections varies in a range of 0.5 to 6 MPa, wherein a stiffness for the cylindrical sections varies in a range of 20 to 100 Mpa, while preserving that the mechanical strength of the proximal and distal cylindrical sections is higher than the mechanical strength of the intermediary cylindrical section.

9. The engineered medical osteonecrosis treatment device as set forth in claim 1, wherein the porosity difference changes gradually from the proximal cylindrical section to the intermediary cylindrical section and to the distal cylindrical section, while preserving that the porosity of the proximal and distal cylindrical sections is less than the porosity of the intermediary cylindrical section.

10. The engineered medical osteonecrosis treatment device as set forth in claim 1, wherein the mechanical strength difference changes gradually from the proximal cylindrical section to the intermediary cylindrical section and to the distal cylindrical section, while preserving that the mechanical strength of the proximal and distal cylindrical sections is higher than the mechanical strength of the intermediary cylindrical section.

11. The engineered medical osteonecrosis treatment device as set forth in claim 1, wherein the porosity of the proximal and distal cylindrical section is defined between 0% to 40% and wherein the porosity of the intermediary cylindrical section is defined above 40% to 95%.

12. The engineered medical osteonecrosis treatment device as set forth in claim 1, wherein the porosity of the proximal and distal cylindrical section is defined between 0% to 30% and wherein the porosity of the intermediary cylindrical section is defined above 30% to 95%.

13. The engineered medical osteonecrosis treatment device as set forth in claim 1, wherein the scaffold has a biodegradation rate that matches bone regeneration, wherein the biodegradation rate can be tailored specifically to a patient's needs.

14. The engineered medical osteonecrosis treatment device as set forth in claim 1, wherein the three cylindrical sections each have a biodegradation rate that matches bone regeneration intended and designed for its respective cylindrical sections.

15. The engineered medical osteonecrosis treatment device as set forth in claim 1, wherein the medical device is adapted to fit in a tunnel bored in a femoral head intended for reconstruction of an osteonecrotic area.

16. The engineered medical osteonecrosis treatment device as set forth in claim 1, wherein one or more growth factors or cellular components are added to a surface of the scaffold.

17. The engineered medical osteonecrosis treatment device as set forth in claim 1, wherein the scaffold is a three-dimensionally printed scaffold.

18. The engineered medical osteonecrosis treatment device as set forth in claim 1, wherein the proximal and distal cylindrical sections mimic cortical bone.

19. The engineered medical osteonecrosis treatment device as set forth in claim 1, wherein the proximal cylindrical section mimics a subchondral surface profile.

20. The engineered medical osteonecrosis treatment device as set forth in claim 1, wherein the intermediary cylindrical section is intended to replace trabecular bone of necrotic tissue.

21. The engineered medical osteonecrosis treatment device as set forth in claim 1, wherein the intermediary cylindrical section is a template for vascularization and bone ingrowth.

22. The engineered medical osteonecrosis treatment device as set forth in claim 1, wherein size, porosity and a ceramic content of the device is personalized based on an individual patient's anatomical and physiological condition.

* * * * *